(12) United States Patent  
Galopin et al.

(10) Patent No.: US 7,414,152 B2
(45) Date of Patent: Aug. 19, 2008

(54) N-SUBSTITUTED P-MENTHANE CARBOXAMIDES

(75) Inventors: Christophe C. Galopin, Chesterfield, VA (US); Pablo Victor Krawec, Cincinnati, OH (US); Jay Patrick Slack, Loveland, OH (US); Lori W. Tigani, Salisbury, MD (US)

(73) Assignee: Givaudan, SA, Vernier (CH)

( * ) Notice: Subject to any disclaimer, the term of this patent is extended or adjusted under 35 U.S.C. 154(b) by 0 days.

(21) Appl. No.: 11/437,294

(22) Filed: May 19, 2006

(65) Prior Publication Data

US 2006/0276667 A1 Dec. 7, 2006

Related U.S. Application Data

(63) Continuation-in-part of application No. PCT/CH2004/000646, filed on Oct. 28, 2004.

(60) Provisional application No. 60/523,977, filed on Nov. 21, 2003.

(51) Int. Cl.
*C07C 233/58* (2006.01)
*A61K 31/165* (2006.01)

(52) U.S. Cl. ............... 564/189; 558/414; 558/415; 514/522; 514/613; 514/624

(58) Field of Classification Search .......... 514/613, 514/624, 522; 564/189; 558/414, 415
See application file for complete search history.

(56) References Cited

U.S. PATENT DOCUMENTS

| 4,136,163 A | 1/1979 | Watson et al. |
| 4,150,052 A | 4/1979 | Watson et al. |

FOREIGN PATENT DOCUMENTS

| GB | 1 457 671 A | 12/1976 |
| WO | WO 2005/002582 A2 | 1/2005 |

OTHER PUBLICATIONS

H.R. Watson, et al., New Compounds With the Menthol Cooling Effect, J. Soc. Cosmet. Chem. 29 185 200(1978), p. 185-200.

*Primary Examiner*—Shailendra Kumar
(74) *Attorney, Agent, or Firm*—Curatolo Sidoti Co., LPA; Joseph G. Curatolo, Esq.; Salvatore A. Sidoti, Esq.

(57) ABSTRACT

Cooling compounds are provided having the formula:

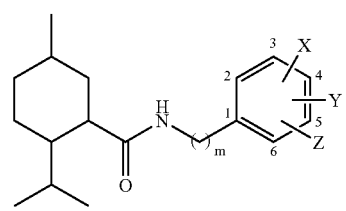

wherein, m is 0 or 1, Y and Z are selected independently from the group consisting of H, OH, C1-C4 straight or branched alkyl, and a C1-C4 straight or branched alkoxy, X is $(CH_2)_n$—R, where n is 0 or 1 and R is a group with non-bonding electrons, with the provisos that: (a) when Y and Z are H, X is not F, OH, MeO or $NO_2$ in the 4-position and is not OH in the 2 or 6-position (b) when Y or Z is H then X, Y and Z are such that
   (i) the groups in the 3- and 4-positions are not both OMe,
   (ii) the groups in the 4- and 5-positions are not both OMe,
   (iii) the groups in 3- and 5-positions are not OMe if the group in the 4-position is OH, and
   (iv) the groups in the 3- and 5-positions are not OH if the group in the 4-position is methyl.

20 Claims, No Drawings

N-SUBSTITUTED P-MENTHANE CARBOXAMIDES

CROSS REFERENCE TO RELATED APPLICATIONS

This application is a continuation-in-part of International Application No. PCT/CH2004/000646 filed Oct. 28, 2004, under 35 USC §120 and §365(c), which claims the benefit of the filing date of U.S. Provisional Application No. 60/523,977 filed Nov. 21, 2003.

COOLING COMPOUNDS ARE PRESENTED

Cooling compounds, that is, chemical compounds that impart a cooling sensation to the skin or the mucous membranes of the body, are well known to the art and are widely used in a variety of products such as foodstuffs, tobacco products, beverages, dentifrices, mouthwashes and toiletries.

One class of cooling compounds that have enjoyed substantial success consists of N-substituted p-menthane carboxamides. Examples of these compounds are described in, for example, British Patents GB 1,351,761-2 and U.S. Pat. No. 4,150,052.

It has now been found that a particular selection of such compounds exhibits a cooling effect that is both surprisingly strong and long-lasting. In one embodiment, the cooling compounds can be represented by formula I

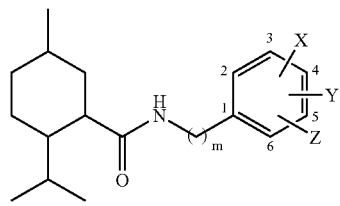

I in which m is 0 or 1, Y and Z are selected independently from the group consisting of H, OH, C1-C4 straight or branched alkyl, and a C1-C4 straight or branched alkoxy; X is $(CH_2)_n$—R, where n is 0 or 1 and R is a group with non-bonding electrons, with the provisos that:
(a) when Y and Z are H, X is not F, OH, MeO or $NO_2$ in the 4-position and is not OH in the 2 or 6-position
(b) when Y or Z is H then X, Y and Z are such that
  (i) the groups in the 3- and 4-positions are not both OMe,
  (ii) the groups in the 4- and 5-positions are not both OMe,
  (iii) the groups in 3- and 5-positions are not OMe if the group in the 4-position is OH, and
  (iv) the groups in the 3- and 5-positions are not OH if the group in the 4-position is methyl.

An embodiment provides for compounds of formula I wherein X is in the 4-position. Additional embodiments provide for compounds of formula I wherein X is in the 4-position and Y and Z are H, OH, Me or OMe. In certain embodiments, Y and Z are selected independently.

Useful groups with non-bonding electrons are halogens, OH, OMe, $NO_2$, CN, Ac, $SO_2NH_2$, CHO, $CO_2H$ and $C_1$-$C_4$ alkyl carboxylates such as $CO_2Et$. Other $C_1$-$C_4$ alkyl carboxylates with non-bonding electrons may be useful.

The compounds of formula I have 3 chiral centres, giving rise to 8 stereoisomers. All possible stereoisomers are included in the scope of the compounds represented by formula I.

The cooling compounds may be prepared by reacting an arylalkylamine derivative with an appropriate acid chloride or carbonyl chloride. The carbonyl chloride can be prepared from 1-menthol ((1R,2S,5R)-2-isopropyl-5-methylcyclohexanol).

The cooling compounds are distinguished from similar compounds of the prior art by their surprisingly high cooling effect (up to 10 times higher than that of similar known compounds) and by the longevity of the cooling effect, which adds to their attractiveness in a large variety of products.

For example, a small group of panelists was asked to taste various solutions of cooling compounds and indicate which solutions had a cooling intensity similar or slightly higher than that of a solution of menthol at 2 ppm. In a second experiment, the same panel was asked to taste the solutions at the chosen concentrations and to record the cooling intensity at regular time intervals until no cooling could be sensed in the mouth. Results are shown in table 1.

TABLE 1 experiment on cooling intensity and longevity.

| Chemical | Concentration | Longevity |
| --- | --- | --- |
| 1-Menthol | 2.0 ppm | 35 minutes |
| N-ethyl p-menthanecarboxamide (WS-3) | 1.5 ppm | 57 minutes |
| Formula I, m = 0, Y = Z = H, X = 4-CN | 0.5 ppm | 90 minutes |
| Formula I, m = 0, Y = Z = H, X = 4-$CH_2CN$ | 0.2 ppm | 93 minutes |

From Table 1, it can be seen that the compounds of Formula I are up to 10 times stronger and last up to 3 times longer than menthol, the reference cooling compound. Compounds of Formula I are also much stronger and last longer than WS-3, a known cooling compound of the prior art.

The subject cooling compounds may be used in products that are applied to the mouth or the skin to give a cooling sensation. By "applying" is meant any form of bringing into contact, for example, oral ingestion or, in the case of tobacco products, inhalation. In the case of application to the skin, it may be, for example, by including the compound in a cream or salve, or in a sprayable composition. A method is directed to providing a cooling effect to the mouth or skin by applying thereto a product comprising a compound as hereinabove described.

The subject cooling compounds may be used alone or in combination with other cooling compounds known in the art, e.g., menthol, menthone, isopulegol, N-ethyl p-menthanecarboxamide (WS-3), N,2,3-trimethyl-2-isopropylbutanamide (WS-23), menthyl lactate (Frescolat™ ML), menthone glycerine acetal (Frescolat™ MGA), mono-menthyl succinate (Physcool™), mono-menthyl glutarate, O-menthyl glycerine (CoolAct™ 10), menthyl-N,N-dimethylsuccinamate or 2-sec-butylcyclohexanone (Freskomenthe™).

The subject cooling compounds and related methods are further described by the following non-limiting examples.

The starting compound p-menthane-3-carbonyl chloride as used for the preparation of the compounds in Example 1-6 was prepared from 1-menthol.

EXAMPLE 1

Preparation of N-(4-cyanomethylphenyl) p-menthanecarboxamide

To a flask, were added 6.6 g (50 mmol) of 4-aminobenzyl cyanide, 4.04 mL of pyridine and 100 mL MtBE. To this mixture, 10 g of p-menthane-3-carbon*yl chloride were added dropwise over 5 minutes. The reaction mixture was stirred for 24 h. To the reaction mixture, 50 mL of water were added. The mixture was separated. The organic layer was washed with 50 mL of water and 50 mL of brine. The organic layer was dried over $MgSO_4$. The solvent was evaporated in vacuo to afford the crude product, which was recrystallized from hexanes to afford 10.1 g of the desired product with the following spectroscopic properties:

MS: 299 ([M+1]), 298 ([M$^+$]), 132, 83. $^1$H NMR (300 MHz; CDCl$_3$) δ: 7.58 (d, 2H), 7.49 (s, 1H), 7.27 (d, 2H), 3.73 (s, 2H), 2.2 (t, 1H), 1.96-1.57 (m, 5H), 1.48-1.21 (m, 2H), 1.172-0.99 (m, 2H), 0.94 (d, 3H), 0.93 (d, 3H), 0.85 (d, 3H). $^{13}$C NMR (75 MHz; CDCl$_3$)δ: 174.4, 137.8, 128.3, 125.1, 120.3, 118.2, 50.5, 44.3, 39.25, 34.3, 32.1, 28.7, 23.8, 22.9, 22.1, 21.2, 16.1

EXAMPLE 2

Preparation of N-(4-sulfamoylphenyl) p-menthanecarboxamide

A preparation similar to that described in example 1 gives the desired product with the following spectroscopic properties:

MS: 339 ([M+1]), 338 ([M$^+$]), 172, 83. $^1$H NMR (300 MHz; DMSO) δ: 10.21 (s, 1H), 7.76 (d, 1H) 7.73 (d, 2H), 7.23 (s, 2H), 2.26-2.42 (m, 1H), 1.45-1.85 (m, 5H), 1.29-1.44 (m, 2H), 0.89 (d, 3H), 0.86 (d, 3H), 0.78 (d, 3H). $^{13}$C NMR (75 MHz; DMSO) δ: 174.6, 142.3, 138.3, 126.7, 118.8, 48.9, 43.7, 34.3, 31.9, 28.6, 23.7, 22.35, 21.3,16.25

EXAMPLE 3

Preparation of N-(4-cyanophenyl) p-menthanecarboxamide

A preparation similar to that described in example 1 gives the desired product with the following spectroscopic properties:

MS: 285 ([M+1]), 284 ([M$^+$]), 139, 83. $^1$H NMR (300 MHz; CDCl$_3$) δ: 7.69 (d, 2H), 7.6 (d, 2 H), 7.5 (s, 1H), 1.85-1.97 (m, 1H), 1.69-1.84 (m, 3H), 1.55-1.69 (m, 2H), 1.21-1.47 (m, 2H), 0.979-1.16 (m, 2H), 0.95 (d, 3H), 0.93 (d, 3H), 0.82 (d, 3H). $^{13}$C NMR (300 MHz; CDCl$_3$) δ: 174.6, 133.1, 119.4, 118.7, 100.35, 50.7, 44.4, 39.25, 34.2, 32.1, 28.8, 23.7, 22.0, 21.2, 16.1, 14.0

EXAMPLE 4

Preparation of N-(4-acetylphenyl) p-menthanecarboxamide

A preparation similar to that described in example 1 gives the desired product with the following spectroscopic properties:

MS: 302 ([M+1]), 301 ([M$^+$]), 135, 83. $^1$H NMR (300 MHz; CDCl$_3$) δ: 7.93 (d, 2H), 7.66 (d, 2H), 7.63 (s, 1H), 2.57 (s, 3H), 2.09-2.31 (m, 1H), 1.84-1.98 (m, 1H), 1.68-1.85 (m, 5H), 1.56-1.68 (m, 1H), 1.17-1.48 (m, 2H), ), 0.93 (d, 3H), 0.91 (d, 3H), 0.83 (d, 3H). $^{13}$C NMR (75 MHz; CDCl$_3$) δ: 197.1, 174.9, 142.7, 129.9, 119.2, 51.2, 44.9, 39.8, 34.8, 32.6, 29.2, 26.6, 24.3, 22.4, 21.5, 16.6

EXAMPLE 5

Preparation of N-(4-hydroxymethylphenyl) p-menthanecarboxamide

A preparation similar to that described in example 1 gives the desired product with the following spectroscopic properties:

MS: 290 (M+1), 289 (M$^+$), 123, 83. $^1$HNMR (300 MHz, DMSO) δ: 9.9 (s, 1H), 7.54 (d, 2H), 7.21 (d, 2H), 4.2 (s, 2H), 2.36-2.1 (m, 1H), 1.8-1.59 (m, 6H), 1.57-1.44 (m, 1H), 1.21-0.9 (m, 4H), 0.87 (dd, 3H), 0.85 (dd, 3H), 0.79 (d, 2H). $^{13}$C NMR (75 MHz; DMSO) δ: 173.7, 137.7, 137.1, 126.7, 118.9, 62.6, 48.6, 43.6, 34.2, 31.7, 28.3, 23.6, 22.2, 21.1, 16.1

EXAMPLE 6

Preparation of N-(3-hydroxy-4-methoxyphenyl) p-menthanecarboxamide

A preparation similar to that described in example 1 gives the desired product with the following spectroscopic properties:

MS: 306 ([M+1]), 305 ([M$^+$]), 139, 83. $^1$H NMR (300 MHz; CDCl$_3$) δ: 7.14 (s, 1H), 7.08 (d, 1H), 6.78 (d, 1H), 5.7 (s, 1H), 3.8 (s, 3H), 2.02-2.21 (m, 2H), 1.53-1.94 (m, 5H), 1.17-1.48 (m, 2H), 0.97-1.17 (m, 2H), 0.92 (dd, 3H), 0.91 (dd, 3H), 0.82 (d, 3H). $^{13}$C NMR (75 MHz; CDCl$_3$) δ: 173.9, 145.6, 143.3, 131.7, 111.65, 110.8, 107.4, 56.1, 50.5, 44.4, 39.2, 32.15, 34.4, 28.6, 23.8, 22.1, 21.2, 16.1

EXAMPLE 7

Application in Mouthwash

| | |
|---|---|
| Alcohol 95% | 177 mL |
| Sorbitol 70% | 250 g |
| Compound of example 1 as a 1% solution in alcohol | 50 mL |
| Peppermint oil, Terpeneless | 0.300 g |
| Methyl salicylate | 0.640 g |
| Eucalyptol | 0.922 g |
| Thymol | 0.639 g |
| Benzoic acid | 1.500 g |
| Pluronic ™ F127 | 5.000 g |
| Sodium Saccharin | 0.600 g |
| Sodium Citrate | 0.300 g |
| Citric Acid | 0.100 g |
| Water | q.s. 1 liter |

The ingredients are mixed. 30 mL of obtained solution is put in the mouth, swished around, gargled and spit out. An intense cooling is felt in every area of the mouth as well as the lips. The cooling perception lasts for several hours.

EXAMPLE 9

Application in Toothpaste

Opaque toothgel 97.000 g
Compound of example 2 as a 2% solution in PG 2.500 g
Peppermint oil, Terpeneless 0.500 g The materials are mixed in the toothgel, and a panelist's teeth are brushed using this toothgel. The mouth is rinsed with water and the water spit out. An intense cooling sensation is felt by the panelist in all areas of the mouth. The cooling perception lasts for several hours.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

What is claimed is:

1. A compound selected from the group consisting of N-(4-cyanomethylphenyl) p-menthanecarboxamide, N-(4-sulfamoylphenyl) p-menthanecarboxamide, N-(4-cyanophenyl) p-menthanecarboxamide, N-(4-acetylphenyl) p-menthanecarboxamide, N-(4-hydroxymethylphenyl) p-menthanecarboxamide and N-(3-hydroxy-4-methoxyphenyl) p-menthanecarboxamide.

2. A method of providing a cooling effect to the mouth or skin by applying thereto a product comprising a compound according to claim 1.

3. A product that is applied to the mouth or the skin comprising an amount of a compound according to claim 1, wherein the amount is effective to give a cooling sensation to the mouth or the skin.

4. A compound comprising formula I

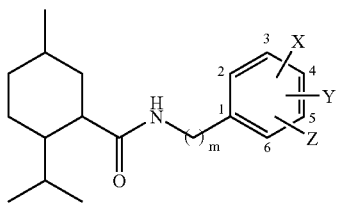

I in which m is 0 or 1, Y and Z are selected independently from the group consisting of H, OH, C1-C4 straight or branched alkyl, and C1-C4 straight or branched alkoxy; X is $(CH_2)_n$—R, where n is 0 or 1 and R is a group with non-bonding electrons; said compound selected from the group consisting of N-(4-cyanomethylphenyl) p-menthanecarboxamide, N-(4-sulfamoylphenyl) p-menthanecarboxamide, N-(4-cyanophenyl) p-menthanecarboxamide, N-(4-acetylphenyl) p-menthanecarboxamide, N-(4-hydroxymethylphenyl) p-menthanecarboxamide and N-(3-hydroxy-4-methoxyphenyl) p-menthanecarboxamide.

5. A method of providing a cooling effect to the mouth or skin by applying thereto a product comprising a compound according to claim 4.

6. A product that is applied to the mouth or the skin comprising an amount of a compound according to claim 4, wherein the amount is effective to give a cooling sensation to the mouth or the skin.

7. The product of claim 6 comprising at least one of foodstuffs, tobacco products, beverages, dentifrices, mouthwashes, or toiletries.

8. The product of claim 7 comprising a cream or salve.

9. The product of claim 7 comprising a sprayable composition.

10. The product of claim 6 further comprising an additional cooling compound.

11. The product of claim 10 wherein the additional cooling compound comprises at least one of menthol, menthone, isopulegol, N-ethyl p-menthanecarboxamide, N,2,3-trimethyl-2-isopropylbutanamide, menthyl lactate, menthone glycerine acetal, mono-menthyl succinate, mono-menthyl glutarate, O-menthyl glycerine, menthyl-N,N-dimethylsuccinamate or 2-sec-butylcyclohexanone.

12. The method of claim 5 wherein said applying comprises inhalation.

13. The method of claim 5 wherein said applying comprises oral ingestion.

14. The product of claim 3 comprising at least one of foodstuffs, tobacco products, beverages, dentifrices, mouthwashes, or toiletries.

15. The product of claim 14 comprising a cream or salve.

16. The product of claim 14 comprising a sprayable composition.

17. The product of claim 3 further comprising an additional cooling compound.

18. The product of claim 17 wherein the additional cooling compound comprises at least one of menthol, menthone, isopulegol, N-ethyl p-menthanecarboxamide, N,2,3-trimethyl-2-i sopropylbutanami de, menthyl lactate, menthone glycerine acetal, mono-menthyl succinate, mono-menthyl glutarate, O-menthyl glycerine, menthyl-N,N-dimethylsuccinamate or 2-sec-butylcyclohexanone.

19. The method of claim 2 wherein said applying comprises inhalation.

20. The method of claim 2 wherein said applying comprises oral ingestion.

* * * * *